United States Patent
Freitag et al.

(10) Patent No.: US 9,783,737 B2
(45) Date of Patent: *Oct. 10, 2017

(54) AMINO TERMINATED PHOSPHONAMIDE OLIGOMERS AND FLAME RETARDANT COMPOSITIONS THEREFROM

(75) Inventors: Dieter Freitag, Krefeld (DE); Marc-Andre Lebel, Boxborough, MA (US); Lawino Kagumba, Cambridge, MA (US); Marc E. Lebel, Boxborough, MA (US); Peter S. Schuler, Westwood, MA (US)

(73) Assignee: FRX POLYMERS, INC., Chelmsford, MA (US)

( * ) Notice: Subject to any disclaimer, the term of this patent is extended or adjusted under 35 U.S.C. 154(b) by 998 days.

This patent is subject to a terminal disclaimer.

(21) Appl. No.: 13/294,796

(22) Filed: Nov. 11, 2011

(65) Prior Publication Data

US 2012/0119172 A1 May 17, 2012

Related U.S. Application Data

(60) Provisional application No. 61/412,612, filed on Nov. 11, 2010.

(51) Int. Cl.
| | |
|---|---|
| *C09K 21/12* | (2006.01) |
| *C07F 9/44* | (2006.01) |
| *C09D 5/18* | (2006.01) |
| *C08G 18/38* | (2006.01) |
| *C08K 5/00* | (2006.01) |

(52) U.S. Cl.
CPC ............ *C09K 21/12* (2013.01); *C07F 9/4407* (2013.01); *C07F 9/4419* (2013.01); *C07F 9/4465* (2013.01); *C07F 9/4476* (2013.01); *C08G 18/3889* (2013.01); *C09D 5/18* (2013.01); *C08K 5/0066* (2013.01)

(58) Field of Classification Search
CPC ...... C09K 21/12; C08G 18/3889; C09D 5/18; C08K 5/0066

See application file for complete search history.

(56) References Cited

U.S. PATENT DOCUMENTS

| | | | |
|---|---|---|---|
| 3,450,677 A | 6/1969 | McConnell et al. | |
| 4,207,721 A | 6/1980 | Raudat et al. | |
| 4,403,075 A | 9/1983 | Byrd et al. | |
| 4,668,720 A | 5/1987 | Kauth et al. | |
| 4,701,554 A * | 10/1987 | Kauth ................... | C08G 79/02 528/398 |
| 5,393,621 A | 2/1995 | Chaloner-Gill | |
| 5,409,976 A | 4/1995 | Lindsay | |
| 5,973,041 A | 10/1999 | Campbell et al. | |
| 6,221,939 B1 | 4/2001 | Campbell et al. | |
| 6,291,700 B1 | 9/2001 | Cella et al. | |
| 7,888,534 B2 | 2/2011 | Freitag et al. | |
| 7,928,259 B2 | 4/2011 | Freitag et al. | |

FOREIGN PATENT DOCUMENTS

| | | |
|---|---|---|
| EP | 0171730 A1 | 2/1986 |
| JP | H071995-041598 | 10/1995 |
| JP | 2001-139823 A | 5/2001 |
| WO | WO 93-22373 | 11/1993 |

OTHER PUBLICATIONS

Office Action dated Sep. 16, 2014 for corresponding Chinese Application No. 2011800648150.
Supplementary European Search Report dated Jan. 31, 2014 for EP 11839579.
International Search Report dated May 21, 2012 for PCT/US2011/060428.

* cited by examiner

*Primary Examiner* — Nicholas Hill
(74) *Attorney, Agent, or Firm* — Pepper Hamilton LLP

(57) ABSTRACT

The invention relates to the use of amino terminated phosphonamides and their oligomers, as flame retardant additives for a variety of polymers to impart flame retardancy while maintaining or improving processing characteristics and other important properties.

27 Claims, No Drawings

AMINO TERMINATED PHOSPHONAMIDE OLIGOMERS AND FLAME RETARDANT COMPOSITIONS THEREFROM

CROSS-REFERENCE TO RELATED APPLICATIONS

This application claims priority from U.S. Provisional Application No. 61/412,612 entitled "Amino Terminated Phosphonamide Oligomers and Flame Retardant Compositions Therefrom" filed Nov. 11, 2010, which is herein incorporated by reference in its entirety.

GOVERNMENT RIGHTS

This invention was developed with Government support under Contract No. FA8650-07-C-5907 awarded by the Department of the Air Force. The Government has certain rights in the invention.

PARTIES TO A JOINT RESEARCH AGREEMENT

Not applicable.

INCORPORATION BY REFERENCE OF MATERIAL SUBMITTED ON A COMPACT DISC

Not applicable.

BACKGROUND

The phosphorus content of polymer compositions is important to achieving flame retardancy. High molecular weight polyphosphonamides often have poor solubility or miscibility in the host polymer, and due to their high melt viscosity, significantly detract from the melt processability of the host resin. When added to thermosetting polymers, a reduction in glass transition temperature (Tg), heat distortion temperature (HDT), and modulus often results. Additionally, adding high molecular weight polyphosphonamides to other polymers leads to a lower phosphorus content compared to using oligomers.

Amino terminated phosphonamide oligomers can react with a variety of monomers and oligomeric species to form copolymers. For example, they can be co-reacted with epoxy formulations to produce a flame retardant polymer in which the phosphonamide oligomer is chemically incorporated into the matrix via covalent bond formation. Likewise, the amino terminated phosphonamide oligomers can be used as reactants to form copolyamides, copolyureas, copolyimides and any other copolymers that can react with an amine functional group. Therefore, there is a need for phosphonamides prepared by any synthetic route that have reactive amino end groups at sufficient concentration to participate in bond forming reactions with other monomers or reactive species to form copolymers.

SUMMARY OF THE INVENTION

Embodiments described herein include a composition comprising an amino terminated phosphonamide of general Formula I:

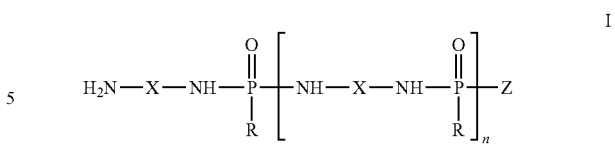

where R is a $C_1$ to $C_{20}$ alkyl or, optionally substituted, aryl group, X is an aromatic or aliphatic group, Z is:

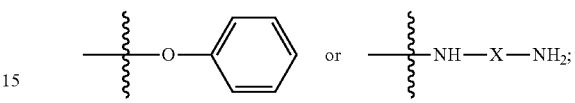

and
n is an integer of from 1 to about 20. In some embodiments, n can be an integer of from 1 to about 10. In other embodiments, the amino-terminated phosphonamide may include at least about 50% amine end-groups based on the total number of end groups. In certain embodiments, R may be methyl, and in some embodiments, each —NH—X—NH— can be derived from a diamine, a triamine, or a polyamine.

Other embodiment are directed to compositions including an amino terminated phosphonamide of general Formula II:

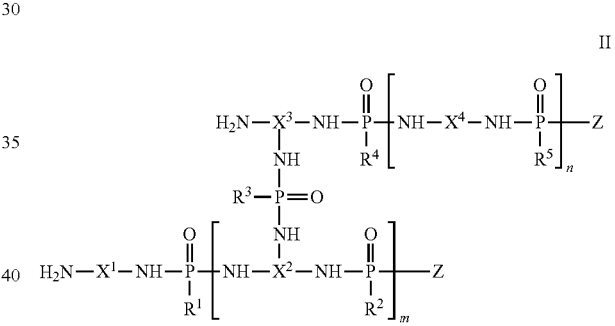

where each of $R^{1-5}$ is individually a $C_1$ to $C_{20}$ alkyl or, optionally substituted, aryl group, each of $X^{1-4}$ is individually, an aromatic, cycloalkyl, or aliphatic group, n and m are each individually an integer of from 0 to about 20 and each Z is, independently:

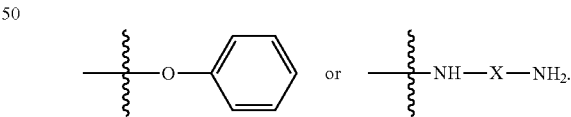

In some embodiments, each m and n are each individually integers from 0 to about 10. In other embodiments, the amino-terminated phosphonamide includes at least about 50% amine end-groups based on the total number of end groups. In particular embodiments, each of $R^{1-5}$ can be methyl, and in other embodiments, each of —NH—$X^{1-4}$—NH— can independently derived from a diamine, a triamine, or a polyamine.

Further are directed to compositions that include the amino terminated phosphonamide of the invention including those of Formulae I and II and one or more polycarbonates, epoxy derived polymers, polyepoxies, benzoxazines, polyacrylates, polyacrylonitriles, polyesters, poly(ethylene terephthalate)s, poly(trimethylene terephthalate) and poly(butylene terephthalate)s, polystyrenes, polyureas, polyurethanes, polyphosphonates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, and combinations thereof, and in some embodiments, these compositions may further include one or more fillers, fibers, surfactants, organic binders, polymeric binders, crosslinking agents, coupling agents, additional flame retardants, anti-dripping agents, anti-static agents, catalysts, colorants, inks, dyes, antioxidants, stabilizers, or combinations thereof.

Still further embodiments are directed to methods for preparing the oligomeric amino terminated phosphonamides of the invention including those of general Formulae I and II, and methods for preparing compositions including the oligomeric amino terminated phosphonamides and another thermoplastic or thermoset resin. Additional embodiments including articles of manufacture and various coatings and moldings created from the oligomeric amino terminated phosphonamides of the invention and compositions including these oligomeric amino terminated phosphonamides.

DESCRIPTION OF DRAWINGS

Not applicable.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that, as used herein and in the appended claims, the singular forms "a", "an", and "the" include plural reference unless the context clearly dictates otherwise. Thus, for example, reference to "a combustion chamber" is a reference to "one or more combustion chambers" and equivalents thereof known to those skilled in the art, and so forth.

As used herein, the term "about" means plus or minus 10% of the numerical value of the number with which it is being used. Therefore, about 50% means in the range of 45%-55%.

The terms "flame retardant," "flame resistant," "fire resistant," or "fire resistance," as used herein, means that the composition exhibits a limiting oxygen index (LOI) of at least 27. "Flame retardant," "flame resistant," "fire resistant," or "fire resistance," may also refer to the flame reference standard ASTM D6413-99 for textile compositions, flame persistent test NF P 92-504, and similar standards for flame resistant fibers and textiles. Fire resistance may also be tested by measuring the after-burning time in accordance with the UL test (Subject 94). In this test, the tested materials are given classifications of UL-94 V-0, UL-94 V-1 and UL-94 V-2 on the basis of the results obtained with the ten test specimens. Briefly, the criteria for each of these UL-94-V-classifications are as follows:

UL-94 V-0 the average burning and/or glowing time after removal of the ignition flame should not exceed 5 seconds and none of the test specimens should release and drips which ignite absorbent cotton wool.

UL-94 V-1: the average burning and/or glowing time after removal of the ignition flame should not exceed 25 seconds and none of the test specimens should release any drips which ignite absorbent cotton wool.

UL-94 V-2: the average burning and/or glowing time after removal of the ignition flame should not exceed 25 seconds and the test specimens release flaming particles, which ignite absorbent cotton wool.

Fire resistance may also be tested by measuring after-burning time. These test methods provide a laboratory test procedure for measuring and comparing the surface flammability of materials when exposed to a prescribed level of radiant heat energy to measure the surface flammability of materials when exposed to fire. The test is conducted using small specimens that are representative, to the extent possible, of the material or assembly being evaluated. The rate at which flames travel along surfaces depends upon the physical and thermal properties of the material, product or assembly under test, the specimen mounting method and orientation, the type and level of fire or heat exposure, the availability of air, and properties of the surrounding enclosure. If different test conditions are substituted or the end-use conditions are changed, it may not always be possible by or from this test to predict changes in the fire-test-response characteristics measured. Therefore, the results are valid only for the fire test exposure conditions described in this procedure. The state-of-the-art approach to rendering polymers flame retardant is to use additives such as brominated compounds or compounds containing aluminum and/or phosphorus. Use of these additives can have a deleterious effect on the processing characteristics and/or the mechanical performance of products produced from them. In addition, some of these compounds are toxic, and can leach into the environment over time making their use less desirable. In some countries certain brominated additives and aluminum and/or phosphorus containing additives are being phased-out of use because of environmental concerns.

Embodiments of the invention are generally directed to amino-terminated phosphonamides, and in some embodiments oligomeric amino terminated phosphonamides. Other embodiments are directed to methods for producing amino terminated phosphonamides. Further embodiments are directed to methods for using amino terminated phosphonamides in thermoset resins, and certain embodiments are directed to thermoplastics having amino terminated phosphonamides and oligomeric amino terminated phosphonamides incorporated into the polymer matrix. Still further embodiments are directed to articles of manufacture that include these thermoplastics having amino terminated phosphonamides and oligomeric amino terminated phosphonamides incorporated into the polymer matrix.

Embodiments are not limited to particular phosphonamides. Various known phosphonamides can be reformulated to include amino termini and are encompassed by the invention. In particular embodiments, the amino terminated phosphonamides of the invention may have the structure of general Formula I:

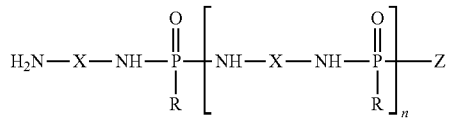

where R is a $C_1$ to $C_{20}$ alkyl or, optionally substituted aryl group, X is an aromatic, cycloalkylene, or aliphatic group, n is an integer of from 1 to about 20, and Z is:

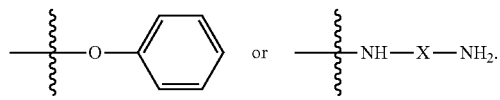

In other embodiments, the predominately amino terminated phosphonamide oligomers may include compounds of Formula II:

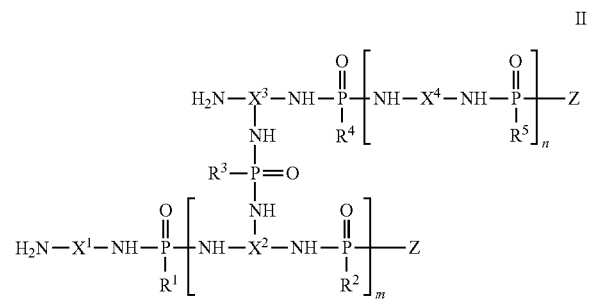

where $R^{1-5}$ are each individually a $C_1$ to $C_{20}$ alkyl or, optionally substituted, aryl group, $X^{1-4}$ are each individually, an aromatic, cycloalkylene, or aliphatic group, n and m are an integer of from 0 to about 20, and each Z is, independently:

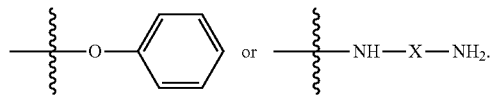

In some embodiments, m and n may each independently be from about 0 to about 10. In other embodiments, m may be an integer of from 0 to about 4, such that the branching, or potential branching, and n may be any integer from 1 to about 10.

In particular embodiments, each —NH—X—NH— provided in Formulae I and II, including the amine containing moieties including X1-4, may be derived from an amine containing monomer including all known diamine, triamine, or polyamine containing monomer. In certain embodiments, each —NH—X—NH— may be derived from the same amine containing monomer, and in other embodiments, each —NH—X—NH— may be derived from two or more different amine containing monomers. Exemplary amine containing monomers include alkanediamines, alkanetriamines, arylamines, cycloalkylamines, or any combinations thereof, and in various embodiments, the alkanediamines, alkanetriamines, arylamines, cycloalkylamines may have from about 6 to about 12 or about 20 carbon atoms. In particular embodiments, the alkanediamines, alkanetriamines, arylamines, cycloalkylamines may have from about 6 to about 8 carbon atoms. More specific non-limiting examples of suitable diamines, triamines, and polyamines include m-xylylenediamine, di(4-aminophenyl)methane, di(4-aminocyclohexyl)methane, 2,2-di(4-aminophenyl)propane, 1,4-diaminobutane, 1,3-bis(aminomethyl)-cyclohexane, 1,4-bis(aminomethyl)-cyclohexane, 2,5-bis(aminomethyl)-bicyclo-[2,2,1]heptane and/or 2,6-bis-(aminomethyl)-bicyclo[2,2,1]heptane, bis-(4-aminocyclohexyl)-derivative of an alkane having from 1 to 6 carbon atoms, and p-xylylene-diamine 2,2-di(4-aminocyclohexyl)propane, and triamine derivatives of these diamines, any mixtures, or combinations thereof. In certain embodiments, —NH—X—NH— may be derived from polyether amine or JEFFAMINE, which are described herein below.

The weight average molecular weight (Mw) of these predominately amino terminated phosphonamide oligomers can vary based on the number of monomers incorporated into the polymer chain and can be form about 200 g/mole to about 10,000 g/mole or about 500 g/mole to about 7,500 g/mole in embodiments (all expressed against polystyrene (PS) standards). The term "predominately" as used herein is meant to infer that at least 50% of the available end groups include an amine group, and in some embodiments, predominately may refer to phosphonamides having from about 50% to about 100%, about 60% to about 90%, about 60% to about 80%, or any range between these exemplary ranges of amine end groups based on the total number of available end groups.

The predominately amino terminated phosphonamide oligomers of such embodiments may be prepared by combining an amine containing monomer and a phosphonate containing monomer and heating this mixture under vacuum. In some embodiments, the reaction mixture may further include a polymerization catalyst such as, for example, magnesium chloride. In general, the vacuum may be sufficient to remove volatile components, such as phenol, produced as the phosphonamide oligomer is made. In some embodiments, the vacuum may be applied in a step wise manner, in which the vacuum is increased and the pressure of the reaction is reduced one or more times, during the polymerization process, and in other embodiments, the pressure may be gradually reduced throughout the polymerization. In still other embodiments, the vacuum may be increased and the pressure reduced both step wise and gradually in the same polymerization method. For example, in some embodiments, the vacuum may be applied to produce an initial pressure of from about 250 mmHg to about 50 mmHg and the pressure may be reduced gradually, in a step wise manner, or both to from about 10 mmHg to about 5 mmHg. In other exemplary embodiments, the initial pressure may be from about 250 mmHg to about 150 mmHg, and this pressure may be reduced to from about 40 mmHg to about 80 mmHg and then reduced again to about 20 mmHg to about 5 mmHg to produce a method with 3 vacuum steps. Other methods may include more than 3 steps, and still other methods may include less than 3 steps, for example, pressure may be gradually reduced throughout polymerization from about 250 mmHg or 150 mmHg to about 10 mmHg or about 5 mmHg.

The temperature of the reaction may be maintained at any temperature at which polymerization may occur. For example, in some embodiments, the reaction temperature may be from about 175° C. to about 300° C., and in other embodiments, the reaction temperature may be from about 200° C. to about 250° C. or 275° C. In some embodiments, a constant reaction temperature may be maintained throughout the polymerization, and in other embodiments, the reaction temperature may change at various times throughout the polymerization reaction. In particular embodiments, the reaction temperature may be increased at steps as the pressure is decreased. For example, in the context of the exemplary embodiments above, the initial reaction temperature may be about 175° C. to about 220° C. when the pressure is from about 250 mmHg to about 150 mmHg. The reaction temperature may be increase to from about 200° C. to about 230° C. when the pressure reduced to from about 40 mmHg to about 80 mmHg, and the reaction temperature may be increased to from about 220° C. to about 275° C. when the pressure is reduced to about 20 mmHg to about 5 mmHg.

The reaction time may be any amount of time necessary to provide sufficient polymerization and may vary with reactants, catalysts, reaction temperatures and pressures, and so on. The skilled artisan may vary the reaction time according to such considerations. In general, the total reaction time may be from about 10 hours to about 40 hours, and in some embodiments, the total reaction time may be from about 15 hours to about 25 hours. The reaction time for various steps or temperature and pressure intervals may also vary, and each step or interval may individually be from about 2 hours to about 20 hours. In certain embodiments, a lower temperature, higher pressure first step or interval may be from about 2 hours to about 6 hours in length, followed by a longer 10 hour to 25 hour step or interval where the temperature is increased and the pressure is reduced. As discussed above, the reaction time for each step or interval may vary and can be determined by the skilled artisan.

In some embodiments, the amine containing monomer may be provided in a molar excess to increase the number of amine end-groups on the phosphonamide oligomers. As discussed above the amine containing monomer may be any diamine, triamine, or polyamine known in the art. In particular embodiments, the amine containing monomer may be provided in a molar excess of at least 10%, and in other embodiments, the amine containing monomer may be provided in a molar excess of from about 10% to about 50%, about 10% to about 30%, or about 10% to about 25%. Without wishing to be bound by theory, when an amine containing monomer is combined with a phosphodiester containing monomer and is provided in a molar excess of 10%, the resulting oligomeric phosphonamide may have about 5% excess amino end-groups versus phosphonate-ester end groups. In still other embodiments, the reaction mixture may include a branching agent, and the ratio of amine to phosphodiester containing monomers may be adjusted to ensure excess amine end-groups in the resulting oligomeric phosphonamide.

In further embodiments, the amino terminated phosphonamides described above can be prepared by reacting diamines, triamines, polyamines, or combinations thereof with phosphinic dihalides.

In various embodiments, amine containing monomer may be any known diamine, triamine, or polyamine containing monomer. Exemplary amine containing monomers include alkanediamines, alkanetriamines, arylamines, cycloalkylamines, or any combinations thereof, and in various embodiments, the alkanediamines, alkanetriamines, arylamines, cycloalkylamines may have from about 6 to about 12 or about 20 carbon atoms. In particular embodiments, the alkanediamines, alkanetriamines, arylamines, cycloalkylamines may have from about 6 to about 8 carbon atoms. More specific non-limiting examples of suitable diamines, triamines, and polyamines include m-xylylenediamine, di(4-aminophenyl)methane, di(4-aminocyclohexyl)methane, 2,2-di(4-aminophenyl)propane, 1,4-diaminobutane, 1,3-bis-(aminomethyl)-cyclohexane, 1,4-bis(aminomethyl)-cyclohexane, 2,5-bis(aminomethyl)-bicyclo-[2,2,1]heptane and/or 2,6-bis-(aminomethyl)-bicyclo[2,2,1]heptane, bis-(4-aminocyclohexyl)-derivative of an alkane having from 1 to 6 carbon atoms, and p-xylylene-diamine 2,2-di(4-aminocyclohexyl)propane, and triamine derivatives of these diamines, any mixtures, or combinations thereof.

In particular embodiments, the amine containing monomer may be polyether amines such as JEFFAMINEs. JEFFAMINEs are well known in the art and any polyether amine or JEFFAMINE can be used to prepare the phosphonamide oligomers of the invention. In particular embodiments, the amine containing monomer may be a JEFFAMINE of the structures provided below.

| Name | Structure | x | Ave Mw |
|---|---|---|---|
| D230 | 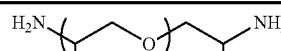 | ~2.5 | 230 |
| D2000 | | ~33 | 2000 |
| T403 | 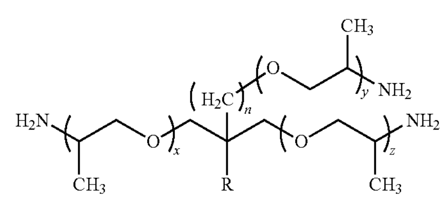 | n = 1<br>(x + y + z) = 5 − 6<br>R = CH$_2$CH$_3$ | 440 |

In certain embodiments, the phosphonate containing monomer may be a diaryl alkyl- or arylphosphonates or optionally substituted diaryl alkyl- or arylphosphonates of embodiments may be of general formula (I):

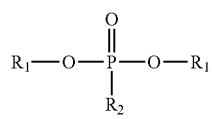

(I)

where $R_2$ may be $C_1$-$C_{20}$ alkyl or, optionally substituted, aryl and $R_1$ may be an aryl group, or a substituted aryl group of formula (II):

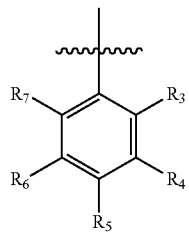

(II)

where $R_3$, $R_4$, $R_5$, $R_6$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, $C_1$-$C_{20}$ alkyl ester, benzyl halide, benzyl ether, aromatic or aryl ether, or optionally substituted versions of these, and $R_3$, $R_4$, $R_5$, $R_6$, and $R_7$ are essentially unaffected by the reaction. In certain embodiments, the diaryl alkylphosphonate may be diphenyl methylphosphonate.

The amino terminated phosphonamides and oligomeric amino terminated phosphonamides described above may include at least one amino termini, and in certain embodiments, the amino terminated phosphonamides and oligomeric amino terminated phosphonamides may have two or more amino termini. In some embodiments, the molecular weight of the oligomeric amino terminated phosphonamides may be substantially the same. In other embodiments, the oligomeric amino terminated phosphonamides may be present in a statistical mixture of various molecular weight species. In such statistical mixtures, an amino group is present of both ends of the same molecule, one end of the molecule, or on neither end of different molecules.

The oligomeric amino-terminated phosphonamides described herein overcome the problems of toxicity and leaching while satisfying the UL or comparable standardized flame resistance rating performance requirements without detracting from important physical, mechanical and processing properties. This is achieved by formulating a composition of a reactive monomer, oligomer or polymer and an effective amount of an amino terminated phosphonamide oligomer. The amount of the amino terminated phosphonamide may be provided in any appropriate flame retarding amount and can range up to about 50% by weight of the final composition, and in some embodiments, the amount of amino terminated phosphonamide may be from about 10% to about 30%, by weight of the final composition. In some embodiments, the oligomeric amino-terminated phosphonamide can be cured with the host resin, and in other embodiments, the oligomeric amino terminated can be pre-reacted with the host resin.

The amino terminated phosphonamide oligomers of various embodiments can be combined with a variety of other monomers, oligomers, and polymers including, for example, epoxies, ureas, esters, urethanes, and imides. In certain embodiments, the amino terminated phosphonamides and oligomeric amino terminated phosphonamide oligomers may be incorporated into thermoplastic and thermosetting polymers such as, but not limited to, polyester, polycarbonate, polyacrylate, polyacrylonitrile, polystyrene (including high impact strength polystyrene and syndiotactic polystyrene), polyurea, polyurethane, linear and branched polyphosphonates, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, epoxies and polyepoxies, such as polymers resulting from the reaction of one or more epoxy monomers or oligomers with one or more chain extenders or curing agents such as a mono or multifunctional phenol, amine, benzoxazine, anhydride or combination thereof, benzoxazine, polyphosphate, cellulose polymer, or any combination thereof. These exemplary thermoplastics and thermosets are well known commercially available commodity engineering plastics that used in a variety of applications. Embodiments of the invention encompass any other such engineering plastics not specifically included in the above lists, and combinations of various thermoplastics and thermoset resins.

In some embodiments, the compositions including a thermoplastic or thermoset resin and an amino-terminated phosphonamide or an oligomeric amino-terminated phosphonamide may further include other additives such as, for example, one or more curing agents, additional flame retardant additives, fillers, anti-dripping agents, and other additives typically used with such polymers. In some embodiments, the additional flame retardant additive may be a complementary flame retardant such as, but not limited to, alumina trihydrate, magnesium hydroxide, organic sulfonate or sulfonamidate salts, siloxanes, (organic) phosphinate salts, metal phosphinate salts, ammonium polyphosphate, melamine, melamine phosphate, melamine pyrophosphate, melamine polyphosphate, melamine cyanurate, red phosphorus, (poly)phosphonates, triphenyl phosphate, or a bisphosphate flame retardant (such as resorcinol bis(diphenyl phosphate), or bisphenol A bis(diphenyl phosphate).

In certain embodiments, the amino terminated phosphonamide or oligomeric amino-terminated phosphonamide may be formulated as fiber reinforced composites. Such fiber reinforced composites may include any of the thermoplastics or thermosets described herein in combination with a fiber or fabric that may be composed of carbon, glass, organic fibers such as polyester, polyaramide, inorganic fibers may include, but are not limited to, silicon carbide. In some embodiments, the reinforcing fiber or fabric may be incorporated into the polymer matrix with the amino terminated phosphonamide or oligomeric amino-terminated phosphonamide, and in other embodiments, the polymer resin, amino terminated phosphonamide or oligomeric amino-terminated phosphonamide can be used to impregnate a reinforcing fiber or fabric.

In particular embodiments, the oligomeric amino-terminated phosphonamide may be provided in epoxy formulations. Such embodiments are not limited to any particular type of epoxy. For example, the epoxy resin may be a bisphenol A epoxy, bisphenol F epoxy, phenolic novolak epoxy, cresol novolak epoxy, bisphenol A novolak epoxy resins, and the like. In some embodiments, the epoxy resins used in embodiments may be halogenated, and in other embodiments, the epoxy resins may be non-halogenated. Such epoxy resins may be used in any application. The epoxies of such embodiments including oligomeric amino-terminated phosphonamides may be incorporated into, for example, circuit boards, housing for electronic components, epoxy encapsulant compositions for use in electronic applications, and in other embodiments, epoxy compositions of the invention can be used for structural applications and as coatings. The oligomeric amino-terminated phosphonamides can be used in place of brominated flame retardants or other phosphorus containing flame retardants, or the oligomeric amino-terminated phosphonamides can be used in combination with such compositions. In some embodiments, epoxy resins compositions including oligomeric amino-terminated phosphonamides may contain other components conventionally used epoxies such as, but not limited to, polyphenylene oxide, imide, phenolic, and benzoxazine resins as well as reinforcement additives such as paper, glass fibers, organic fibers, or carbon fibers.

In some embodiments, the oligomeric amino-terminated phosphonamide of the invention may be used in combination with polyurea. The oligomeric amino-terminated phosphonamides can be incorporated into any polyurea formulation known in the art. For example, in certain embodiments, the polyurea formulations may include diisocyanates, aromatic or aliphatic diamines, or combinations thereof in addition to the amino terminated phosphonamide.

In some embodiments, the oligomeric amino-terminated phosphonamide may be used in crosslinked polymer compositions. In some embodiments, an oligomeric amino-terminated phosphonamides having two or more functional amine groups per oligomer chain such as, but not limited to, those described in Formula I and Formula II can act as a crosslinking agent. These oligomeric amino-terminated phosphonamides can be combined with a thermoplastic or thermoset resin having functional groups that can react with the amine groups of the oligomeric amino-terminated phosphonamide. For example, in particular exemplary embodiments, crosslinked polyureas can be produced by combining polyureas with the amino terminated phosphonamides of embodiments of the invention, and, for example, triisocyanates, diisocyanates, aromatic or aliphatic diamines, or combinations thereof.

In some embodiments, the oligomeric amino terminated phosphonamides can be mixed or blended with other monomers, oligomers, or polymers and these mixtures can be used for preparing articles of manufacture from the blended material. For example, some embodiments include methods for preparing a polymer composition including the steps of blending in a melt a monomer, oligomer, or polymer and a oligomeric amino terminated phosphonamide. The melt blending may be carried out by any mixing technique, for example, melt mixing may be carried out in a brabender mixer or extruder. In some embodiments, the methods may include the steps of extruding the mixture after melt mixing and pelletizing the resulting material. In other embodiments, the methods may include compressing the melt mixed material in rollers to create a film, spincasting a film, blowmolding a film or extruding a sheet product. In still other embodiments, the methods may include molding the melt mixed material into an article of manufacture. In still other embodiments the oligomeric amino terminated phosphonamide can be mixed in solution with other components and, optionally after mixing with another solution, be sprayed to form a film.

Still other embodiments include polymeric compositions prepared from these amino terminated phosphonamide oligomers and other monomers, oligomers or polymers that meet UL fire or comparable standardized fire resistance ratings required for a variety of consumer products without detracting from other important safety, environmental, manufacturing and consumer use requirements. For example, consumer electronics must meet particular fire resistance standards as specified by the Underwriter's Laboratory (UL) or comparable standardized fire resistance rating criteria without compromising other properties such as Tg, HDT, and interfacial adhesion. The electronics often contain circuit boards that include epoxy/glass laminates. The state-of-the-art approach to rendering these systems flame retardant is to use various additives such as brominated compounds or compounds containing aluminum, antimony, and/or phosphorus. However, these compounds are often toxic, and can leach into the environment over time making their use less desirable. In some countries these additives and related additive types are being phased out of use.

Further embodiments include articles of manufacture that include a polymer matrix and the amino terminated phosphonamide or oligomeric amino-terminated phosphonamide of the invention. For example, certain embodiments are directed to consumer electronics and other consumer products that must meet particular fire resistance standards as specified by UL or other standardized criteria. Such consumer electronics and consumer products may contain or include, for example, circuit boards, housings, or other components or subcomponents that include amino terminated phosphonamide or oligomeric amino-terminated phosphonamide containing compositions, filled amino terminated phosphonamide or oligomeric amino-terminated phosphonamide containing compositions, or fiber reinforced amino terminated phosphonamide or oligomeric amino-terminated phosphonamide compositions. The components fabricated from such compositions will generally meet the UI-94 V-0 or similar criteria for fire resistance while retaining good properties such as Tg, HDT, interfacial adhesion, and the like.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Materials

JEFFAMINE diamines (D230, D2000 and T403) were purchased from Huntsman Petrochemical Corporation. Expandable graphite—GRAFGUARD® 160-50 was obtained from GrafTech International. Ammonium polyphosphonate (APP) (20 µm powder) was obtained from ICL-LP. Diphenyl methyl phosphonate (DPP) was prepared using methods referred to in U.S. Pat. No. 7,888,534 B2 and U.S. Pat. No. 7,928,259 B2, Dragonshield-BC (DSBC™) was obtained from Specialty Products Inc. (SPI).

Example 1

Preparation of Oligomeric Amino Terminated Phosphonamides

The reactions of various aromatic and aliphatic diamines with diphenylmethyl phosphonate were carried out in a round bottom flask fitted with a mechanical stirrer, $N_2$/vacuum inlet, and a distillation column (filled with hollow glass tubes) wrapped with electrical heating tape. The reagents were heated to 200° C. for 12-14 hrs., while gradually lowering the vacuum from 400 mmHg to 5 mmHg. The temperature was then increased to 240° C. for 4-6 hrs at <1 mmHg (full vacuum) to drive off residual phenol and any unreacted starting materials. The amino terminated phosphonamide product was isolated as a viscous liquid. The reaction was monitored by gas chromatography-mass spectroscopy (GC-MS) by analysis of the phenol by-product. The amino terminated phosphonamide oligomer was analyzed using nuclear magnetic resonance spectroscopy ($^1$H-NMR) and the % phosphorus was determined using inductively coupled plasma optical emission spectrometry (ICP-OES).

Example 2

Synthesis of an Amino Terminated Phosphonamide 276.0 g (1.2 mol) JEFFAMINE D230, 297.8 g (1.2 mol) DPP and 3.05 g (0.03 mol) magnesium chloride were added to a 1 L round bottom flask and heated to 200° C. while stirring for 14 hours. The vacuum was gradually lowered to 60 mmHg over 6 hrs., maintained at 40 mm Hg for 4 hrs, and then lowered to 10 mmHg for 4 hrs. The distillation column was maintained at 115° C. for 14 hrs. The distillate was collected in a flask cooled in ice. After 14 hours, full vacuum was applied (<0.5 mmHg) and the temperature increased to 240° C. for 2.5 hrs. The product was isolated as a highly viscous liquid (320.6 g). GC-MS analysis of the distillate indicated the total phenol collected was 170.3 g (1.8 mol), residual diamine 23.2 g (0.1 mol) and residual DPP collected was 53.7 g (0.2 mol). Anal. % P=10.6 wt. %.

Example 3

Synthesis of an Amino Terminated Phosphonamide 301.3 g (1.31 mol) JEFFAMINE D230, 259.3 g (1.05 mol) DPP and 3.05 g (0.03 mol) magnesium chloride were added to a 1 L round bottom flask and heated to 200° C. while stirring for 19 hours. The vacuum was gradually lowered to 60 mmHg over 9 hrs., and then lowered to 3.0 mmHg over 5 hrs. and held for 4 hrs. The distillation column was maintained at 115° C. The distillate was collected in a flask cooled in ice. After 19 hours, full vacuum was applied (<0.5 mm Hg) and the temperature increased to 230° C. for 1 hr. The product was isolated as a highly viscous liquid (276.3 g). GC-MS analysis of the distillate indicated the total phenol collected was 178.3 g (1.9 mol), residual diamine 66.7 g (0.3 mol) and residual DPP collected was 24.5 g (0.1 mol). Molecular weight (Mw 670, Mn 570) (GPC, PS standards). Anal. % P=10.4 wt. %.

Example 4

Synthesis of an Amino Terminated Phosphonamide 956.2 g (0.48 mol) JEFFAMINE D2000, 109.2 (0.44 mol) DPP and 2.67 g (0.028 mol) magnesium chloride were added to a 3 L round bottom flask and heated to 200° C. while stirring for 18.5 hours. The vacuum was gradually lowered to 20 mmHg over 3 hrs. and held for 11.5 hrs., and then to 5 mm Hg for 4 hrs. The distillation column was maintained at 115° C. for 6.5 hrs. and then increased to 140° C. The distillate was collected in a flask cooled in ice. After 18.5 hrs., full vacuum was applied (<0.5 mm Hg) for 4.5 hrs. at 200° C. Then, the temperature increased to 215° C. for 1.0 hr., and to 240° C. for 2.5 hrs. The product was isolated as a highly viscous liquid (969 g). GC-MS analysis of the distillate indicated the total phenol collected was 66.2 g (0.7 mol), and residual DPP collected was 13.6 g (0.05 mol). Anal. % P=1.3 wt. %.

Example 5

Synthesis of an Amino Terminated Phosphonamide 175.0 g (0.39 mol) JEFFAMINE T403, 124.1 g (0.5 mol) DPP and 1.24 g (0.013 mol) magnesium chloride were added to a 500 mL round bottom flask and heated to 200° C. while stirring for 7 hours. The vacuum was gradually lowered to 55 mmHg over 2 hrs, then to 5 mm Hg over 5 hrs. The distillation column was maintained at 115° C. The distillate was collected in a flask cooled in ice. After 7 hrs., full vacuum was applied (0.1 mm Hg) for 2 hrs at 200° C., and then increased to 250° C. for 2 hrs. After 2 hrs. the product cross-linked in the flask and the reaction was discontinued. The product was removed from the flask by breaking the flask and 48.1 g of solid was recoverable. Total phenol collected was 73.0 g (0.8 mol), and residual unreacted triamine 9.6 g (0.02 mol) and 17.6 g DPP (0.07 mol). Anal. % P=6.5 wt %.

Example 6

Synthesis of an Amino Terminated Phosphonamide 175.0 g (0.39 mol) JEFFAMINE T403, 124.1 g (0.5 mol) DPP and 1.24 g (0.013 mol) magnesium chloride were added to a 500 mL round bottom flask and heated to 200° C. while stirring for 14 hours. The vacuum was gradually lowered to 25 mmHg over 3 hrs., then to 5 mm Hg for 11 hrs. The distillation column was maintained at 115° C. The distillate was collected in a flask cooled in ice. After 14 hrs., full vacuum was applied (<0.5 mm Hg) for 4.5 hrs. at 200° C. The product was isolated as a solid (219.1 g). GC-MS analysis of the distillate indicated the total phenol collected was 72.3 g (0.8 mol), and no residual triamine or DPP was collected. Anal. % P=7.3 wt. %.

Example 7

Synthesis of an Amino Terminated Phosphonamide 1789 g (0.90 mol) JEFFAMINE D2000, 203 g (0.82 mol) DPP and 0.5 g (0.005 mol) magnesium chloride were added to a 3 L round bottom flask and heated to 200° C. while stirring under vacuum (250 mmHg). After 4.5 hrs, the vacuum was gradually lowered to 10 mmHg over 8 hrs. and then to 5 mm Hg for 4 hrs. After 16.5 hrs., full vacuum was applied (<0.5 mm Hg), and the temperature increased to 225° C. for 1.0 hr. and then to 240° C. for 3.5 hrs. The distillation column was maintained at 115° C. for 16.5 hrs. and then increased to 140° C. The distillate was collected in a flask cooled in ice. The product was isolated as a highly viscous liquid (1855 g). GC-MS analysis of the distillate indicated the total phenol collected was 123.6 (1.31 mol), and residual DPP collected was 0.4 g (0.002 mol). Anal. % P=1.3 wt. %.

Example 8

Synthesis of an Amino Terminated Phosphonamide 1789 g (0.90 mol) JEFFAMINE D2000, 203 g (0.82 mol) DPP and 0.5 g (0.005 mol) magnesium chloride were added to a 3 L round bottom flask and heated to 200° C. while stirring under vacuum (250 mmHg). After 4.5 hrs., the vacuum was gradually lowered to 10 mmHg over 8 hrs and then to 5 mm Hg for 4 hrs. After 16.5 hrs., full vacuum was applied (<0.5 mm Hg), and the temperature increased to 225° C. for 1.0 hr., and then to 240° C. for 3.5 hrs. The distillation column was maintained at 115° C. for 16.5 hrs. and then increased to 140° C. The distillate was collected in a flask cooled in ice. The product was isolated as a highly viscous liquid (1843 g). GC-MS analysis of the distillate indicated the total phenol collected was 90.2 g (0.96 mol), and residual DPP collected was 19.0 g (0.08 mol). Anal. % P=1.3 wt. %.

Example 9

Amino Terminated Phosphonamide Oligomers in Polyureas

Polyurea formulations are generally prepared by the reaction of diamines with diisocyanates. In order to produce flame retardant polyureas, several phosphorus based diamines (FZX diamines) were prepared and added to the diamine formulations used to prepare blast mitigation coatings. (Scheme 1).

Scheme 1. Flame Retardant (FR) Copoly (Urea Phosphonamide) Chemistry

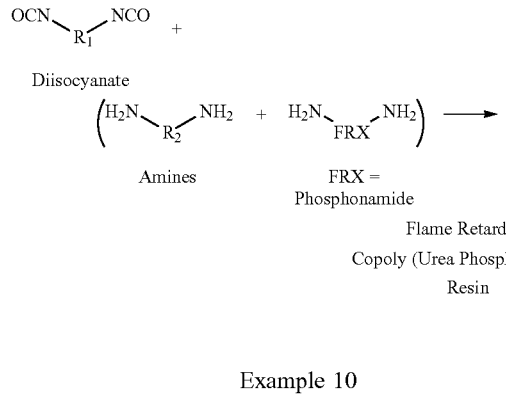

Example 10

Polyurea Films with Amine Terminated Phosphonamide Oligomers

Polyurea films were prepared by spraying out a combination of diisocyanates (A-side) and diamines (B-side) onto primed concrete boards of 6 inches×18 inches for flammability testing. The thickness of each coating was 90 mils (0.09 inches). The test was conducted in accordance with the ASTM E-162, "Standard Method of Test for Surface Flammability of Materials Using a Radiant Heat Energy Source." The spray-coated boards are mounted in a frame placed facing the radiant panel, but inclined at an angle of 30 degrees from top downward. A pilot burner adjusted to provide a 6" to 7" flame serves to ignite the sample at the top. The material under test burns downward.

Oligomeric amine terminated phosphonamides were added to the B-side of the mixture during formulation. Phosphorus-based additives—diphenyl methylphosphate (DPP) and ammonium polyphosphate (APP)—were also tested as additives in the A-side and the B-side, respectively. Graphite was added to various formulations to prevent dripping during burning. The base formulation was Dragonshield BC™ (DSBC™).

DSBC™ Formulations containing the commercial flame retardant additive ammonium polyphosphonate (APP) were prepared and evaluated in comparison to phosphonamide oligomers. Due to processability during formulation, the optimal loading of the amine-terminated phosphonamide oligomer PA-D2000 was 17 wt. %.

Tables 1-2 provide results from ASTM E162 testing of the FR polyurea samples. The results are recorded as a Flamespread Index determined from progression time of the flame at 3, 6, 9, 12, and 15 inch interval marks measured from the top of the sample. The maximum temperature increase resulting from the burning sample was measured by 8 thermocouples connected in parallel and located in the sheet metal stack above the tested sample. The Flamespread Index (FSI) is derived by the following formula:

$$Is = Fs \times Q$$

where Is is the Flamespread Index, Fs is the Flamespread Factor, and Q is the Heat Evolution Factor. The flamespread classification system used by most of the model building codes and the National Fire Protection Association Life Safety Code, NFPA No. 101, encompasses the following:

Class A (I)—0 to 25 Flamespread Index
Class B (II)—26 to 75 Flamespread Index
Class C (III)—76 to 100 Flamespread Index The results of FSI testing of various polyurea compositions including oligomeric amino-terminated phosphonamides are provided in Table 1.

TABLE 1

Polyurea FR Testing: Flame Spread Index (FSI) Results

Wt % Additives in DSBC ™ Formulation

| # | A-Side DPP | Graphite | B-Side PA-D2000 (Example 3) | APP | Total % P | ASTM E162 | FSI Class |
|---|---|---|---|---|---|---|---|
| 1 | 0 | 0 | 0 | 0 | 0 | 212 | Fail |
| 2 | 0 | 2 | 0 | 10 | 1.0 | 114 | Fail |
| 3 | 0 | 5 | 0 | 10 | 1.0 | 64 | B |
| 4 | 0 | 5 | 0 | 20 | 2.6 | 54 | B |
| 5 | 0 | 5 | 17 | 0 | 0.1 | 89 | C |
| 6 | 8 | 5 | 0 | 10 | 1.5 | 70 | B |
| 7 | 8 | 5 | 17 | 0 | 0.6 | 47 | B |

TABLE 2

Polyurea FR Testing: Flame Spread Index (FSI) Results

Wt % Additives in DSBC ™ Formulation

| # | A-Side DPP | Graphite | B-Side PA-D2000 (Example 6) | APP | Total % P | ASTM E162 | FSI Class |
|---|---|---|---|---|---|---|---|
| 1 | 0 | 0 | 0 | 0 | 0 | 212 | Fail |
| 2 | 0 | 10 | 0 | 2 | 0.3 | 34 | B |
| 3 | 8 | 10 | 17 | 2 | 0.9 | 13 | A |

Example 11

Evaluation of FR Behavior of Phosphonamides in Bisphenol-A Epoxies

The FR performance of cured epoxy resin samples with and without phosphonamides was evaluated, and the results are provided in Table 3. The samples were prepared by mixing the amine-terminated phosphonamide oligomers with the epoxy resin and curing in an oven at 60° C. for 48 hr. The FR was evaluated by holding a flame to the sample for 10 seconds and observing for self-extinguishing behavior. The formulation containing the amine terminated phosphonamide oligomer (PA-D230 Example 2) exhibited self-extinguishing behavior, whereas the formulation containing the diamine (D230) continued to burn.

TABLE 3

Epoxy formulations with phosphonamides

| Amine-terminated compound | D230 | PA-D230 (Example 2) |
|---|---|---|
| Weight (g) | 6.5 | 6.5 |
| Epoxy resin (g) | 5 | 5 |
| Diethyl triamine (g) | 0 | 0.5 |
| Total % P | 0 | 5.6 |
| FR evaluation—Self-extinguishing | no | yes |

The invention claimed is:

1. A composition comprising amino terminated phosphonamides of general Formula I:

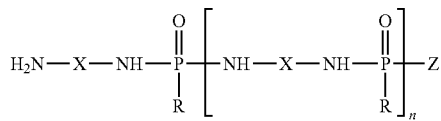

I wherein:
R is a $C_1$ to $C_{20}$ alkyl or, optionally substituted, aryl group;
Z is:

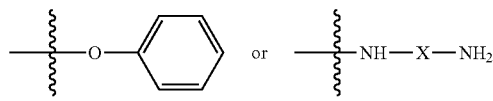

and each —NH—X—NH— is derived from a polyether amine; and
n is an integer of from 1 to about 20; and
wherein at least one amino terminated phosphonamide Z is

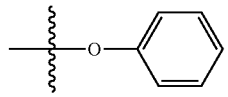 [SMILES: *Oc1ccccc1]

and the amino-terminated phosphonamide comprises at least about 50% amine end-groups based on the total number of end groups.

2. The composition of claim 1, wherein n is an integer of from 1 to about 10.

3. The composition of claim 1, wherein R is methyl.

4. The composition of claim 1, wherein each —NH—X—NH— is derived from a diamine, a triamine, or a polyamine.

5. The composition of claim 1, further comprising one or more monomer, oligomer, or polymer.

6. The composition of claim 1, further comprising one or more polycarbonates, epoxy derived polymers, polyepoxies, benzoxazines, polyacrylates, polyacrylonitriles, polyesters, poly(ethylene terephthalate)s, poly(trimethylene terephthalate) and poly(butylene terephthalate)s, polystyrenes, polyureas, polyurethanes, polyphosphonates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, and combinations thereof.

7. The composition of claim 1, further comprising one or more fillers, fibers, surfactants, organic binders, polymeric binders, crosslinking agents, coupling agents, additional flame retardants, anti-dripping agents, anti-static agents, catalysts, colorants, inks, dyes, antioxidants, stabilizers, or combinations thereof.

8. A composition comprising an amino terminated phosphonamide of general Formula II:

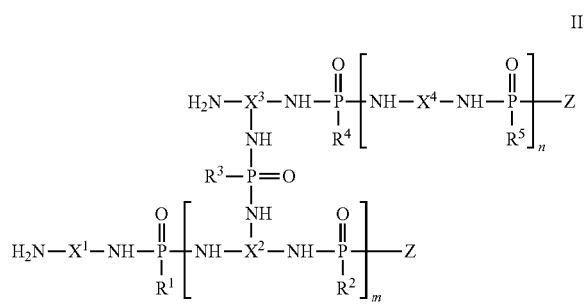

II wherein
each $R^{1-5}$ is individually a $C_1$ to $C_{20}$ alkyl or, optionally substituted, aryl group;
each $X^{1-4}$ is individually, an aromatic, cycloalkyl, polyether, or aliphatic group;
n is an integer of from 0 to about 20; and
m is an integer of 1 to about 10;
each Z is, independently:

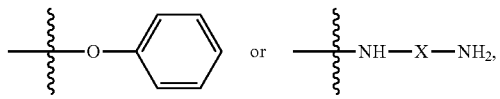

and
X is an aromatic or aliphatic group.

9. The composition of claim 8, wherein n is an integer of from 0 to about 10.

10. The resin composition of claim 9, further comprising one or more fillers, fibers, surfactants, organic binders, polymeric binders, crosslinking agents, coupling agents, additional flame retardants, anti-dripping agents, anti-static agents, catalysts, colorants, inks, dyes, antioxidants, stabilizers, or combinations thereof.

11. The composition of claim 8, wherein the amino-terminated phosphonamide comprises at least about 50% amine end-groups based on the total number of end groups.

12. The composition of claim 8, wherein each $R^{1-5}$ is methyl.

13. The composition of claim 8, wherein each of —NH—$X^{1-4}$—NH— is independently derived from a diamine, a triamine, or a polyamine.

14. The composition of claim 8, wherein each of —NH—$X^{1-4}$—NH— is independently derived from an alkanediamine, alkanetriamine, arylamine, or cycloalkylamine having from about 6 to about 20 carbon atoms.

15. The composition of claim 8, wherein each of —NH—$X^{1-4}$—NH— is independently derived from a polyether amine.

16. The composition of claim 8, further comprising one or more monomer, oligomer, or polymer.

17. The composition of claim 8, further comprising one or more polycarbonates, epoxy derived polymers, polyepoxies, benzoxazines, polyacrylates, polyacrylonitriles, polyesters, poly(ethylene terephthalate)s, poly(trimethylene terephthalate) and poly(butylene terephthalate)s, polystyrenes, polyureas, polyurethanes, polyphosphonates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, and combinations thereof.

18. The composition of claim 8, further comprising one or more fillers, fibers, surfactants, organic binders, polymeric binders, crosslinking agents, coupling agents, additional flame retardants, anti-dripping agents, anti-static agents, catalysts, colorants, inks, dyes, antioxidants, stabilizers, or combinations thereof.

19. A resin composition comprising:
units derived from amino terminated phosphonamides of general Formula I:

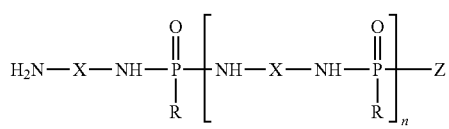

wherein:
R is a $C_1$ to $C_{20}$ alkyl or, optionally substituted, aryl group;
Z is:

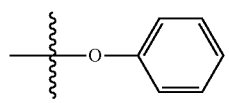

and each —NH—X—NH— is derived from a polyether amine; and
n is an integer of from 1 to about 20; and
wherein at least one amino terminated phosphonamide Z is

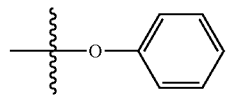

and the amino-terminated phosphonamide comprises at least about 50% amine end-groups based on the total number of end groups; and
one or more monomer, oligomer, or polymer covalently associated with the units derived from the amino terminated phosphonamide.

20. The resin composition of claim 19, wherein the one or more monomer, oligomer, or polymer comprises units derived from a phosphonate, isocyanate, epoxy, carboxylic acid, carboxylic acid ester, or combinations thereof.

21. The resin composition of claim 19, wherein the one or more monomer, oligomer, or polymer comprises one or more polycarbonates, epoxy derived polymers, polyepoxies, benzoxazines, polyacrylates, polyacrylonitriles, polyesters, poly(ethylene terephthalate)s, poly(trimethylene terephthalate) and poly(butylene terephthalate)s, polystyrenes, polyureas, polyurethanes, polyphosphonates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, and combinations thereof.

22. The resin composition of claim 19, further comprising at least one other polymer or oligomer to make a blend or mixture.

23. An article of manufacture comprising amino terminated phosphonamide oligomers of Formula I:

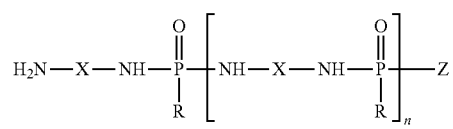

wherein:
R is a $C_1$ to $C_{20}$ alkyl or, optionally substituted, aryl group;
Z is:

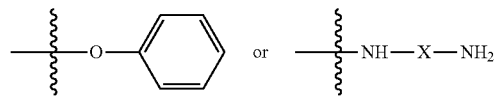

and each —NH—X—NH— is derived from a polyether amine; and
n is an integer of from 1 to about 20; and
wherein at least one amino terminated phosphonamide oligomer Z is

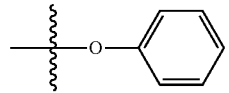

and the amino-terminated phosphonamide comprises at least about 50% amine end-groups based on the total number of end groups.

24. The article of manufacture of claim 23, wherein the article of manufacture comprises a coating, adhesive, prepreg, foam, film, extruded sheet, fiber, molding, fiber reinforced laminate, fiber reinforced circuit board, or combination thereof.

25. The article of manufacture of claim 23, wherein the article of manufacture comprises a consumer product.

26. The article of manufacture of claim 23, wherein the article of manufacture exhibits a limiting oxygen index (LOI) of at least 27.

27. The article of manufacture of claim 23, wherein article exhibits an Underwriters Laboratory-94 (UL-94) of V-0 measured at a thickness of 0.8 mm.

* * * * *